United States Patent [19]

Tanemura et al.

[11] 4,447,453
[45] May 8, 1984

[54] ANTI-PEPTIC ULCER AGENT

[75] Inventors: Mitsura Tanemura, Tokyo; Tamotsu Yamazaki; Koji Mizuno, both of Saitama; Shin-ichi Kaiho, Chiba; Morio Kakimoto; Eiichi Hoshino, both of Saitama; Isao Matsunaga, Tokyo; Shun-ichi Hata, Kanagawa, all of Japan

[73] Assignee: Chugai Seiyaku Kabushiki Kaisha, Tokyo, Japan

[21] Appl. No.: 322,182

[22] Filed: Nov. 17, 1981

[30] Foreign Application Priority Data

Nov. 28, 1980 [JP] Japan ............... 55-166662

[51] Int. Cl.³ .................................. A61K 31/195
[52] U.S. Cl. .......................................... 424/319
[58] Field of Search ............................. 424/319

[56] References Cited

U.S. PATENT DOCUMENTS 4,092,426 5/1978 Tanemura et al. ............... 424/309
4,152,448 5/1979 Wardell ............................ 424/283

Primary Examiner—Frederick E. Waddell
Attorney, Agent, or Firm—Browdy and Neimark

[57] ABSTRACT

An anti-peptic ulcer agent which contains as an active ingredient aminobenzoic acid compounds of the formula

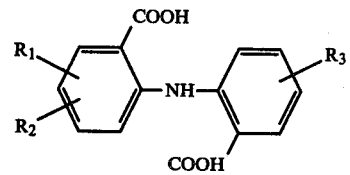

(wherein $R_1$, $R_2$, and $R_3$ which may be the same or different represent a hydrogen atom, halogen atom, lower alkyl group or lower alkoxy group but they do not represent a hydrogen atom at the same time) or pharmaceutically acceptable salts thereof and a method of preventing or treating a human in need of said prevention or treatment an effective amount of said active ingredient are disclosed.

12 Claims, No Drawings

ANTI-PEPTIC ULCER AGENT

FIELD OF THE INVENTION

The present invention relates to an anti-peptic ulcer agent which has as an active ingredient aminobenzoic acid compounds of the formula:

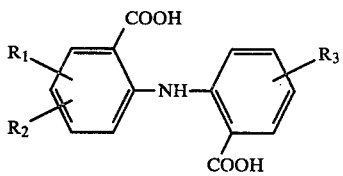

(wherein $R_1$, $R_2$ and $R_3$ which may be the same or different represent a hydrogen atom, halogen atom, lower alkyl group or lower alkoxy group but they do not represent a hydrogen atom at the same time) or pharmaceutically acceptable salts thereof.

The "alkyl group" for $R_1$, $R_2$ and $R_3$ contains from 1 to 4 carbon atoms and is straight or branched chain alkyl group, for example, methyl, ethyl, propyl, isopropyl, butyl, isobutyl.

The "alkoxy group" for $R_1$, $R_2$ and $R_3$ includes a straight or branched chain alkoxy group containing from 1 to 4 carbon atoms, examples of which are methoxy, ethoxy, propoxy, isopropoxy, butoxy, isobutoxy.

The halogen atom for $R_1$, $R_2$ and $R_3$ is fluorine, chlorine, bromine or iodine.

BACKGROUND OF THE INVENTION

The compounds of the formula (I) was produced by the present inventors, and some of them are known to be capable of improving the liver function as well as preventing and treating diseases caused by immunodeficiency (see Japanese Patent Public Disclosure No. 12141/77 and U.S. Pat. No. 4,092,426). Further studies have shown that these compounds also have anti-ulcer activities that are entirely different pharmacological effects from those to improve liver function and immunological function. The present invention is the result of this unexpected finding plus follow-up studies.

DETAILED DESCRIPTION OF THE INVENTION

Some of the compounds according to the present invention are identified below:

| Compound | Melting Point |
|---|---|
| 1. 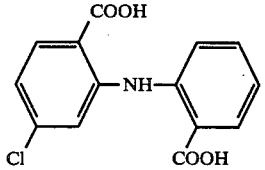 | >340° C. |
| 2. 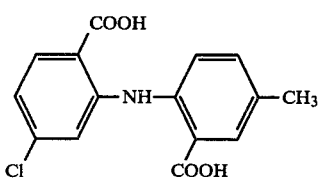 | 316–318° C. with decomposition |
| 3. | >340° C. |
| 4. | >283° C. |
| 5. | 315° C. |
| 6. | >300° C. |
| 7. | 270–271° C. with decomposition |
| 8. | 272–273° C. with decomposition |
| 9. | 288–289° C. with decomposition |
| 10. | 276–278° C. with decomposition |
| 11. | 242–243° C. with decomposition |

-continued

| Compound | | Melting Point |
|---|---|---|
| 12. | 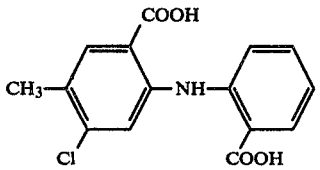 | 276–277° C. with decomposition |
| 13. | 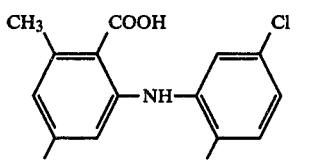 | 254–255° C. with decomposition |
| 14. | 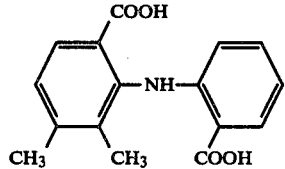 | 276–277° C. with decomposition |
| 15. | 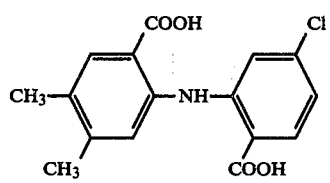 | >280° C. |

These compounds may be formulated in medicines in the form of salts of alkaline earth metals.

The compounds listed above have very low toxicity, and the first six compounds have following the $LD_{50}$ values when they are administered orally to ddY strain male mice (5 weeks old and weighing from 26–30 g) in the form of a suspension in a 2% aqueous gum arabic:

Compound 1: 2100 mg/kg
Compound 2: >1500
Compound 3: >2000
Compound 4: 3000
Compound 5: 1250
Compound 6: >2000

EXAMPLE 1

Groups of 8-week-old Spraque-Dawley male rats each consisting of 10 members were starved for 48 hours, anaethesized with ether and had their pylorus ligated in accordance with the method of Shay et al. (Gasteroenterology, 5, 43–61, 1945). Immediately thereafter, they were administered the compounds of the present invention intra-duodenally or intraperitoneally. Eighteen hours later, they were killed with excess ether and the gastric mucus membrane was removed and observed under a stereoscopic microscope (×10). The diameter (mm) of the ulcers developed in each rat was summed and the sum was used as the ulcer index of each rat. The average ulcer index and inhibition for each group are set forth in Table 1 below.

TABLE 1

| Test compound | Dose (mg/kg) | Intra-duodenal | | Intra-peritoneal | |
|---|---|---|---|---|---|
| | | ulcer index (means ± S.E.) | inhibition (%) | ulcer index (means ± S.E.) | inhibition (%) |
| 2 | 0 (control) | 4.1 ± 0.4 | — | 3.9 ± 0.4 | — |
| | 50 | 0.5 ± 0.3*3 | 87.8 | 0.8 ± 0.4*3 | 80.7 |
| | 100 | 0.3 ± 0.3*3 | 92.7 | — | — |
| | 200 | 0*3 | 100 | — | — |
| 3 | 0 (control) | 4.0 ± 0.3 | — | — | — |
| | 50 | 2.3 ± 0.7*1 | 33.7 | 0.3 ± 0.3*3 | 95.7 |
| | 100 | 0.9 ± 0.6*3 | 78.0 | — | — |
| | 200 | 0*3 | 100 | — | — |
| 5 | 0 (control) | 3.8 ± 0.4 | — | — | — |
| | 50 | 1.3 ± 0.6*3 | 67.1 | 0*3 | 100 |
| | 100 | 0.1 ± 0.1*3 | 96.6 | — | — |
| | 200 | 0*3 | 100 | — | — |
| 6 | 0 (control) | 3.3 ± 0.7 | — | — | — |
| | 50 | 1.4 ± 0.7*2 | 58.6 | 2.0 ± 0.7*1 | 48.6 |
| | 100 | 0.3 ± 0.3*3 | 92.5 | — | — |
| | 200 | 0*3 | 100 | — | — |

*1 $P<0.005$
*2 $P<0.01$
*3 $P<0.001$

EXAMPLE 2

Groups of 7-week-old Sprague-Dawley male rats each consisting of 10 members were starved for 24 hours and administered orally the compounds of the present invention. Ten minutes later, they were confined in a restrainer cage according to the method of Takagi et al. (Japanese Journal of Pharmacology, 18, 9–18, 1968), and the cage was placed vertically in a water tank at 23°–24° C. until the rats were immersed in the water to the depth of the processus xiphoideus. Sixteen hours later, the rats were killed with excess ether and had their stomach removed. Each stomach was incised along the greater curvature after the surface of the gastric mucosa and serous membrane was lightly fixed with 1% formalin. The diameter (mm) of the ulcers developed in each rat was summed and the sum was used as the ulcer index for each rat. The average ulcer index and inhibition for each group are set forth in Table 2 below.

TABLE 2

| Test compound | Dose (mg/kg) | ulcer index (means ± S.E.) | Inhibition (%) |
|---|---|---|---|
| 2 | 0 (control) | 15.5 ± 5.0 | — |
| | 50 | 12.0 ± 6.2 | 22.5 |
| | 100 | 1.7 ± 1.2*2 | 89.2 |
| | 200 | 0*3 | 100 |
| 3 | 0 (control) | 18.7 ± 5.4 | — |
| | 50 | 14.3 ± 3.9 | 23.3 |
| | 100 | 9.4 ± 4.8 | 49.5 |
| | 200 | 1.5 ± 0.8*2 | 92.0 |

TABLE 2-continued

| Test compound | Dose (mg/kg) | ulcer index (means ± S.E.) | Inhibition (%) |
|---|---|---|---|
| 5 | 0 (control) | 15.7 ± 1.2 | — |
|   | 50 | 9.6 ± 4.4 | 38.5 |
|   | 100 | 1.8 ± 0.9*3 | 88.2 |
|   | 200 | 0*3 | 100 |
| 6 | 0 (control) | 18.5 ± 1.7 | — |
|   | 50 | 12.1 ± 3.5 | 34.3 |
|   | 100 | 1.5 ± 1.1*3 | 92.9 |
|   | 200 | 0*3 | 100 |

*2 $p < 0.01$
*3 $p < 0.001$

EXAMPLE 3

The activity of the compounds of the present invention to cure peptic ulcer was measured as in Example 1. The results are shown in Table 3 below. The test compound was administered in the duodenum.

TABLE 3

| Test compound | Dose (mg/kg) | Ulcer index (means ± S.E.) | Inhibition (%) |
|---|---|---|---|
| Control | — | 3.57 ± 0.3 | — |
| 8 | 100 | 0 ± 0*** | 100.0 |
| Control | — | 3.6 ± 0.3 | — |
| 9 | 100 | 0.7 ± 0.7** | 80.1 |
| 10 | 100 | 0 ± 0*** | 100.0 |
| 11 | 100 | 1.4 ± 0.6** | 60.0 |
| 12 | 100 | 0.3 ± 0.3*** | 91.8 |
| Control | — | 2.0 ± 0.4 | — |
| 13 | 100 | 1.0 ± 0.7 | 50.0 |
| 14 | 100 | 0.4 ± 0.4* | 78.5 |

*$p < 0.05$
**$p < 0.01$
***$p < 0.001$

EXAMPLE 4

The activity of the compounds of the present invention to cure peptic ulcer was measured as in Example 2. The results are shown in Table 4 below.

TABLE 4

| Test compound | Dose (mg/kg) | Ulcer index (means ± S.E.) | Inhibition (%) |
|---|---|---|---|
| Control | — | 12.4 ± 2.5 | — |
| 7 | 200 | 0.2 ± 0.1** | 98.4 |
| 8 | 200 | 1.7 ± 1.3** | 96.7 |
| Control | — | 38.6 ± 5.3 | — |
| 9 | 200 | 6.5 ± 3.4*** | 83.4 |
| 10 | 200 | 3.8 ± 1.5*** | 90.1 |
| 11 | 200 | 1.2 ± 0.9*** | 96.9 |
| 12 | 200 | 1.3 ± 0.7*** | 96.7 |
| 13 | 200 | 11.6 ± 6.2** | 70.0 |
| 14 | 200 | 3.5 ± 1.6*** | 90.9 |
| 15 | 200 | 8.2 ± 3.2*** | 78.8 |

*$p < 0.05$
**$p < 0.01$
***$p < 0.001$

As is demonstrated by the data above, the anti-peptic ulcer agent of the present invention is capable of controlling almost completely the ulcers developed in diseased rats such as Shay rats and rats with stress-induced ulcer, and the desired effect is achieved by administering it in an effective dose of 200 mg/kg.

The anti-peptic ulcer agent of the present invention may be formulated as a tablet, granule, powder, capsule or injection by a known method wherein it is mixed with a pharmaceutically acceptable carrier together with an optional adjuvant. Examples of the pharmaceutically acceptable carrier that can be used in the preparation of tablets, granules, powder and capsules are lactose, starch, dextrin, mannitol, sucrose, crystalline cellulose, kaolin, calcium carbonate, talc and magnesium stearate. For preparing an injection, the compounds are preferably dissolved in distilled water or a salt solution of, say, sodium chloride or potassium chloride.

The compounds of the present invention are incorporated in the respective formulations in a unit dose that varies with the age and condition of the patient. For oral administration, the dose is usually from 100 to 1,000 mg/day, preferably from 250 to 750 mg/day, and for intravenous injection, a dose is usually from 10 to 300 mg/day, preferably from 50 to 150 mg/day.

EXAMPLE 5

(a) Preparation of tablet

| | |
|---|---|
| Compound 2 (Na salt) | 100 g |
| Lactose | 46 g |
| Crystalline cellulose | 27 g |
| Corn starch | 5 g |
| Magnesium stearate | 2 g |

The indicated compounds were mixed intimately and compressed into anti-ulcer tablets having a diameter of 8 mm and weighing 180 mg.

(b) Preparation of injection

A mixture of 10 g of Compound 1 (Na salt) and 9 g of sodium chloride was dissolved in distilled water to make one liter which was divided among 2-ml ampules that were closed by fusing then sterilized at 100° C. for 30 minutes to make stable anti-ulcer injections.

What is claimed is:

1. A therapeutic method of treating peptic ulcer which comprises administering to a human in need of said therapy an effective amount for treating peptic ulcer of an active compound of the formula

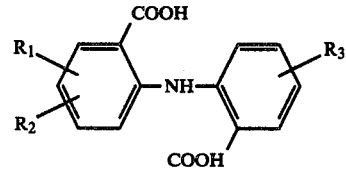

wherein $R_1$, $R_2$ and $R_3$ which may be the same or different represent a hydrogen atom, halogen atom, lower alkyl group or lower alkoxy group but they do not all represent a hydrogen atom at the same time, or pharmaceutically acceptable salt thereof.

2. A method according to claim 1 wherein the active compound is 4-chloro-3-methyl-2,2'-iminodibenzoic acid or its pharmaceutically acceptable salt.

3. A method according to claim 1 wherein the active compound is 3,4-dimethyl-2,2'-iminodibenzoic acid and its pharmaceutically acceptable salt.

4. A method according to claim 1 wherein the active compound is 4-methyl-2,2'-iminodibenzoic acid or its pharmaceutically acceptable salt.

5. A method according to claim 1 wherein the active compound is 4,5-dimethyl-2,2'-iminodibenzoic acid or its pharmaceutically acceptable salt.

6. A method according to claim 1 wherein the active compound is 4-chloro-5-methyl-2,2'-iminodibenzoic acid or its pharmaceutically acceptable salt.

7. A method according to claim 1 wherein the active compound is 4,6-dimethyl-2,2'-iminodibenzoic acid or its pharmaceutically acceptable salt.

8. A method according to claim 1 wherein the active compound is 4-chloro-4'-methoxy-2,2'-iminodibenzoic acid or its pharmaceutically acceptable salt.

9. A method according to claim 1 wherein the active compound is 4,5'-dimethoxy-2,2'-iminodibenzoic acid or its pharmaceutically acceptable salt.

10. A method according to claim 1 wherein the pharmaceutically acceptable salt is a sodium salt.

11. A method according to claim 1 which comprises administering the active compound in an amount of from 100 to 1,000 mg per day for oral administration, or from 10 to 300 mg per day for injection.

12. A method according to claim 11 which comprises administering the active compound in an amount of from 250 to 750 mg per day for oral administration, or from 50 to 150 mg per day for injection.

* * * * *